United States Patent [19]
Li et al.

[11] Patent Number: 5,932,749
[45] Date of Patent: *Aug. 3, 1999

[54] ASYMMETRIC SYNTHESIS OF R-α-PROPYL-PIPERONYL AMINE AND ITS ANALOGS

[75] Inventors: Hui-Yin Li, Newark, Del.; Luigi Anzalone, West Chester, Pa.; Robert Eugene Waltermire, Wilmington, Del.

[73] Assignee: DuPont Pharmaceuticals Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/822,996

[22] Filed: Mar. 21, 1997

Related U.S. Application Data

[60] Provisional application No. 60/013,955, Mar. 22, 1996.
[51] Int. Cl.⁶ .................................................. C07D 317/58
[52] U.S. Cl. ................................................................ 549/440
[58] Field of Search ............................................... 549/440

[56] References Cited

U.S. PATENT DOCUMENTS 5,149,838   9/1992   Humphrey et al. ...................... 549/471

FOREIGN PATENT DOCUMENTS 0481671   4/1992   European Pat. Off. .
3819438   1/1989   Germany .

OTHER PUBLICATIONS

Ukaji et al, Diasterofacial Discrimination in the Reaction of Chiral Alkoxymethyl Oxime Ethers with Allyl Metallic Reagents, *Chemistry Letters* 1991, 173–176.

Wu et al, Synthesis of Chiral α–Alkyl Phenethylamines via Organometallic Addition to Chiral 2–Aryl–1,3–oxazolidines, *J. Org. Chem.* 1991, 56, 1340–1344.

Higashiyama et al, Diastereoselective Addition of Chiral Aliphatic Imines and 2–Alkyl–1,3–Oxazolidines to Organometallic Reagents, *Chem. Pharm. Bull.* 1995, 43(5), 722–728.

Bringmann et al, The Enantioselective Synthesis of Optically Active, Benzene Nucleus–Substituted 1–Phenylethylamines from the Corresponding Acetophenones, *Liebigs Ann. Chem.* 1990, 795–805.

Eleveld et al, Diastereoselective Synthesis of Chiral Secondary Amines with Two Chiral Centers Directly Attached to the Nitrogen Atom, *J. Org. Chem.* 1986, 51, 3635–3642.

Fink et al, Orally Active, Intracellular Inhibitors of Human Leukocyte Elastase (HLE), Abstract #083, 210th ACS Nat'l Mtg., DN of Med. Chem. 1995.

Mascaretti et al, β–Lactam Compounds. Inhibitors of Transpeptidases, β–Lactamases and Elastases: A Review, *Current Medicinal Chemistry* 1995, 1, 441–470.

Peisach et al, Interaction of a Peptidomimetic Aminimide Inhibitor with Elastase, *Science* 1995, 269, 66–69.

Bringmann et al, Enantiomerically Pure Oxygenated 1–Phenylethylamines from Substituted Acetophenones: by Reductive Amination and Regiospecific Benzylic Cleavage, *Tetrahedron Letters* 1989, 30(3), 317–320.

Yoshida et al, Asymmetric Hydrogenation of the C=N Bond. A Study of the Controlling Factors on the Stereoselectivity, *Bull. Chem. Soc. Japan* 1972, 45, 3706–3710.

Bringmann et al, Enantiomerically Pure N–Boc Protected β–Keto–γ–Amino Acid Esters from Simple Keto Precursors: A Novel, Stereocontrolled Approach to Statine Derivatives with Any Desired Configuration, *Synlett* 1990, 253–255.

*Primary Examiner*—Jane Fan
*Attorney, Agent, or Firm*—David H. Vance

[57] ABSTRACT

Processes for the preparation of R-α-propyl-piperonyl amine and its analogs, such compounds being useful intermediates in the preparation of elastase inhibitors, and intermediates useful for making R-α-propyl-piperonyl amine are described.

11 Claims, No Drawings

ASYMMETRIC SYNTHESIS OF R-α-PROPYL-PIPERONYL AMINE AND ITS ANALOGS

This application claims under 35 USC 119 (e) of Mar. 22, 1996 60/013955.

FIELD OF THE INVENTION

The present invention relates generally to processes for the preparation of R-α-propyl-piperonyl amine and its analogs, such compounds being useful intermediates in the preparation of elastase inhibitors, and intermediates useful for preparation of R-α-propyl-piperonyl amine.

BACKGROUND OF THE INVENTION

[S-(R*,S*]N-{1-(1,3-benzodioxol-5-yl)butyl]-3,3-diethyl-2-[4-[(4-methyl-1-piperazinyl)carbonyl]phenoxyl]-4-oxo-1-azetidinecarboxamide (EI) shown below:

EI

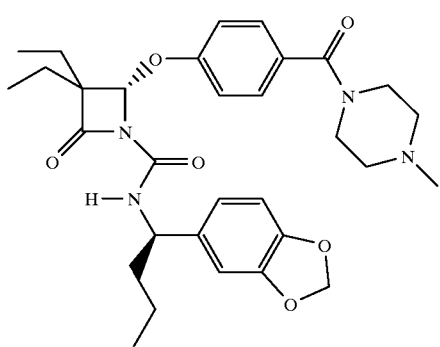

a selective, non-toxic, orally active human elastase inhibitor, is currently being evaluated for treatment of cystic fibrosis. Consequently, large quantities of (EI) are needed to support drug development studies.

Synthetic routes to compounds similar to (EI) have been described; see for example EP 0,481,671, which suggests (EI) could be formed by joining the substituted cyclic lactam portion of (EI) with R-α-propyl-piperonyl via a carbonyl linker. R-α-propyl-piperonyl amine, a chiral amine, could, therefore, be a significant intermediate in this process if an efficient, industrially scalable route were known.

Humphrey et al, in U.S. Pat. No. 5,149,838, discuss formation of (R)-1-(benzo[β]furan-5-yl)-1-aminobutane from 5-bromobenzo[β]furan. The process described involves as a last step the conversion of (S)-1-(benzo[β]furan-5-yl)-1-butanol to (R)-1-(benzo[B]furan-5-yl)-1-aminobutane under Mitsonobu conditions. Unfortunately, side reactions and stereochemical leakage predominated when a Mitsonobu process was applied to the synthesis of R- or S-α-propyl-piperonyl amine, an intermediate useful for making compounds like EI.

Bringmann et al, in DE 3,819,438, describe formation of chiral amines by reacting substituted-aryl ketones with chiral methylbenzylamine, hydrogenating the resulting imine over Ra—Ni, at 1–200 bar and from 20 to 60° C., and removal of the phenethyl group by hydrogenating over Pd/C at 1–200 bar and 20 to 50° C. Bringmann et al, in Tetr. Lett. 1989, 30(3), 317, report reduction of chiral imines formed using S-α-methylbenzylamine by hydrogenating at 5 bar hydrogen with Ra—Ni in EtOH. Bringmann et al, in Synlett 1990, 253, report reduction of chiral imines formed using S-α-methylbenzylamine by hydrogenating at 60 bar with Pd/C or with NaBH₄. In addition, Bringmann et al, in Leibigs Ann. Chem. 1990, 795, detail hydrogenolysis of N-(1-phenylethyl)-1-arylethylamines using either hydrogen and palladium on carbon for three weeks or ammonium formate and palladium on carbon. However, the present inventors have found hydrogenolysis of (R)-N-[1-(1,3-Benzodioxol-5-yl)butylidene]-α-methylbenzenemethanamine using the procedures described by Bringmann et al was either very slow or racemization of R-α-propyl-piperonyl amine occurred.

Eleveld et al, J. Org. Chem 1986, 51, 3635, report the hydrogenation of chiral imines, in particular N-(methyl(o-methoxy)benzylidene)-α-methylbenzyl amine. Hydrogenation with Pd/C and 3 atm hydrogen produced greater than 90% de of the SS isomer. In comparison, the corresponding m-methoxy imine resulted in only a 67% de. The high de obtained with the o-methoxy compound was attributed to the steric hinderance provided by the o-methoxy group. One readily realizes that R- and S-α-propyl-piperonyl amines contain only m-alkoxy groups. Thus, the procedure of Eleveld et al would not be expected to be of use in making R- and S-α-propyl-piperonyl amines.

Ukaji et al, Chem. Lett. 1991, 173, indicated the reaction of oxime ethers with allylmagnesium bromide provided little diastereoselectivity. If the oxime ether was separated into its E and Z isomers, then allylmagnesium bromide complexed with cerium chloride provided de's ranging from 50–72%. Based on this report, one would probably need cerium chloride if a Grignard reaction was used as an intermediate step in the formation of R- or S-α-propyl-piperonyl amine. However, cerium chloride is usually avoided and 50–72% de is rather low.

Wu et al, J. Org. Chem 1991, 56, 1340, report diastereoselective addition of Grignard reagents (e.g., methyl, ethyl and butyl) to 2-aryl-1,3-oxazolidines. Again, cerium trichloride was indicated as enhancing the diastereoselectivity of the Grignard addition. Addition of methylmagnesium bromide to p-methoxyphenyl-4-phenyl-1,3-oxazolidine provided high diastereoselectivity, but only a 45% yield. Such low yields aren't useful for industrial purposes.

Higashiyama et al, Chem. Pharm. Bull. 1995, 43(5), 722, discuss Grignard addition to chiral aliphatic imines derived from (R)—O-methylphenylglycinol. However, cerium trichloride is used. Removal of phenylglycinol was achieved by hydrogenating over palladium hydroxide in ethyl acetate.

Based on the above-noted articles, it would seem to be difficult to efficiently produce R- and S-α-propyl-piperonyl amines on large scale without using undesirable reagents. It is thus desirable to find a new synthetic procedure for industrial scale production of R-α-propyl-piperonyl amine and its analogs.

SUMMARY OF THE INVENTION

Accordingly, one object of the present invention is to provide a novel process for making a compound of Formula I:

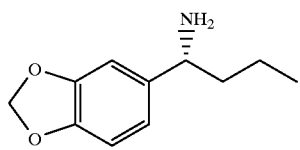

I or stereoisomer or salt forms thereof.

Another object of the present invention is to provide novel compounds of formulae IV and VII, defined below, which are useful intermediates for making compounds of formula I.

These and other objects, which will become apparent during the following detailed description, have been achieved by the inventors' discovery that the compound of Formula I or stereoisomer or salt forms thereof, are formed by a high yielding, regioselective process, comprising:

(a) contacting a compound of Formula II:

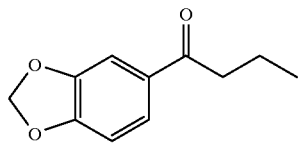

II with a chiral methylbenzylamine to form a compound of Formula

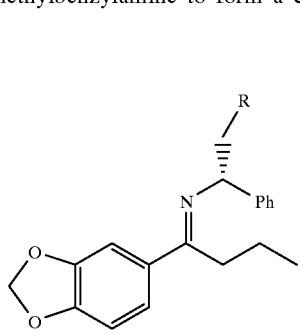

III or stereoisomer thereof, wherein R is selected from H, OH and OCH$_3$;

(b) hydrogenating a compound of Formula III of stereoisomer or salt form thereof in the presence of Ra—Ni to form a compound of Formula IV:

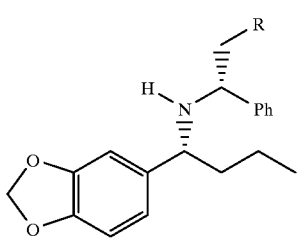

IV or diastereomer or salt form thereof, wherein the hydrogenation is performed under conditions selected from:

(bi) about 0.01–3000 psi of hydrogen at one temperature; or (bii) about 0.01–3000 psi of hydrogen at a first temperature and a second temperature greater than the first temperature; and, (c) hydrogenating a compound of Formula IV or stereoisomer or salt form thereof to form a compound of Formula I or stereoisomer or salt form thereof; or (d) contacting a compound of Formula V:

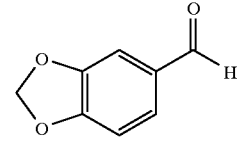

V with a chiral methylbenzylamine to form a compound of Formula VI:

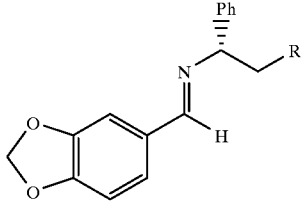

VI or stereoisomer or salt form thereof, wherein R is H, OH, or OCH$_3$;

(e) contacting the compound of Formula VI or stereoisomer or salt form thereof with allylmagnesium bromide to form a compound of Formula VII:

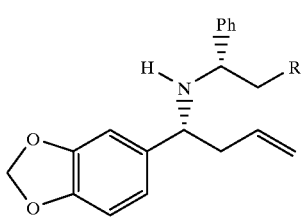

VII or diastereoisomer or salt form thereof, wherein R is H, OH, or OCH$_3$; and, (f) hydrogenating a compound of Formula VII or diastereomer or salt form thereof in the presence of palladium on carbon form a compound of Formula I or stereoisomer or salt form thereof.

DETAILED DESCRIPTION OF THE INVENTION

[1] Thus, in a first embodiment, the present invention provides a process for the synthesis of a compound of Formula I:

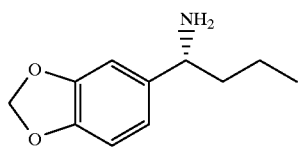

or stereoisomer or salt form thereof, comprising:
(a) contacting a compound of Formula II:

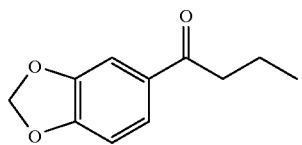

with a chiral methylbenzylamine to form a compound of Formula III:

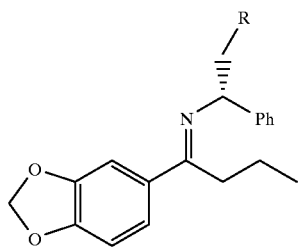

or stereoisomer thereof, wherein R is selected from H, OH and $OCH_3$;

(b) hydrogenating a compound of Formula III of stereoisomer or salt form thereof in the presence of Ra—Ni to form a compound of Formula IV:

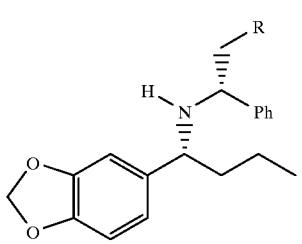

or diastereomer or salt form thereof, wherein the hydrogenation is performed under conditions selected from:
(bi) about 0.01–10 psi of hydrogen at one temperature of from 0–100° C. for about 2–30 hours or 10–3000 psi at one temperature of from 60 to 80° C. for about 2–30 hours; or,
(bii) about 0.01–3000 psi of hydrogen at a first temperature for about 2–8 hours and a second temperature for about 2–24 hours, the first temperature being from 0–35° C. and the second temperature being from 50–100° C.; and,
(c) hydrogenating a compound of Formula IV or stereoisomer or salt form thereof in the presence of palladium on carbon and a solvent selected from an alcohol, a carboxylic acid, a dicarboxylic acid, an aromatic carboxylic acid and mixtures thereof to form a compound of Formula I or stereoisomer or salt form thereof;
provided that the compound of Formula IV hydrogenated in step c is not a hydrogen bromide salt.

[2] In a preferred embodiment, in step (a), the chiral methylbenzylamine is R-α-methylbenzylamine, in step (b) R is H, and in step (c) R is H and the solvent is selected from a $C_{1-3}$ alcohol, a $C_{2-4}$ carboxylic acid, and mixtures thereof.

[3] In a more preferred embodiment, hydrogenation step (b) is performed under conditions (bi); and,
hydrogenation step (c) is performed in a mixture of a $C_{1-3}$ alcohol and a $C_{2-4}$ acid, wherein the alcohol and acid are present in a ratio of from 30:1 to 1:10.

[4] In an even more preferred embodiment, hydrogenation step (bi) is performed under 0.01–2 psi of hydrogen at a temperature of from 20 to 60 20 C. for from 3–24 hours; and,
in hydrogenation step (c), the alcohol is selected from methanol and ethanol, the acid is acetic acid, and the ratio of alcohol to acid is from 30:1 to 1:1.

[5] In a further preferred embodiment, hydrogenation step (bi) is performed under 0.01-1 psi of hydrogen at a temperature selected from ambient temperature or 50 to 60° C. for from 3–12 hours; and,
hydrogenation step (c) is performed in ethanol and acetic acid in a ratio of from 20:1 to 8:1.

[6] In another further preferred embodiment, hydrogenation step (bi) is performed under 0.01-1 psi of hydrogen at a temperature selected from ambient temperature or 50 to 60° C. for from 3–12 hours; and,
hydrogenation step (c) is performed in methanol and acetic acid in a ratio of from 20:1 to 8:1.

[7] In another even more preferred embodiment, in step (c) from 1 to 4 equivalents of acid based on the amount of IV are present.

[8] In another even more preferred embodiment, in step (c) about 2 equivalents of acid based on the amount of IV are present.

[9] In another even more preferred embodiment, hydrogenation step (b) is performed under conditions (bi) under 10–1000 psi hydrogen at a temperature of from 60 to 80° C. for from 3–24 hours.

[10] In another further preferred embodiment, hydrogenation step (bi) is performed under 50–500 psi hydrogen.

[11] In another more preferred embodiment, hydrogenation step (b) is performed under conditions (bii); and,
hydrogenation step (c) is performed in a mixture of a $C_{1-3}$ alcohol and a $C_{2-4}$ acid, wherein the alcohol and acid are present in a ratio of from 30:1 to 1:10.

[12] In an even more preferred embodiment, hydrogenation step (bii) is performed under from 50–500 psi of hydrogen at a first temperature of from 20–30° C. for about 3–6 hours and a second temperature of from 60–80° C. for about 6–18 hours; and,
in hydrogenation step (c), the alcohol is selected from methanol and ethanol, the acid is acetic acid, and the ratio of alcohol to acid is from 30:1 to 1:1.

[13] In an even more preferred embodiment, hydrogenation step (bii) is performed under from 50–500 psi of hydrogen at a first temperature of from 20–30° C. for about 3–6 hours and a second temperature of from 60–80° C. for about 10–15 hours; and,
in hydrogenation step (c), the alcohol is selected from methanol and ethanol, the acid is acetic acid, and the ratio of alcohol to acid is from 30:1 to 1:1.

[14] In a further preferred embodiment, hydrogenation step (bii) is performed under from 100–300 psi of hydrogen at a first temperature which is about ambient temperature for about 3, 4, 5, or 6 hours and a second temperature of from 65–75° C. for about 10, 11, 12, 13, 14, or 15 hours; and, hydrogenation step (c) is performed in ethanol and acetic acid in a ratio of from 20:1 to 8:1.

[15] In a further preferred embodiment, hydrogenation step (bii) is performed under from 100–300 psi of hydrogen at a first temperature which is about ambient temperature for about 3, 4, 5, or 6 hours and a second temperature of from 65–75° C. for about 10, 11, 12, 13, 14, or 15 hours; and, hydrogenation step (c) is performed in methanol and acetic acid in a ratio of from 20:1 to 8:1.

[16] In another even more preferred embodiment, in step (c) about 1 to 4 equivalents of acid based on the amount of IV are present.

[17] In another even more preferred embodiment, in step (c) about 2 equivalents of acid based on the amount of IV are present.

[18] In a second embodiment, the present invention provides a process for the synthesis of a compound of Formula I:

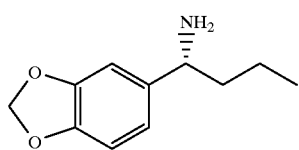

I or stereoisomer or salt thereof, comprising:

(d) contacting a compound of Formula V:

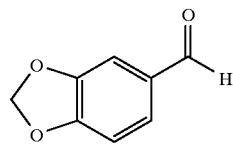

V with a chiral methylbenzylamine to form a compound of Formula VI:

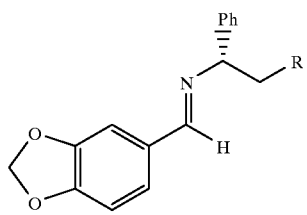

VI or stereoisomer or salt form thereof, wherein R is H, OH, or $OCH_3$;

(e) contacting the compound of Formula VI or stereoisomer or salt form thereof with allylmagnesium bromide to form a compound of Formula VII:

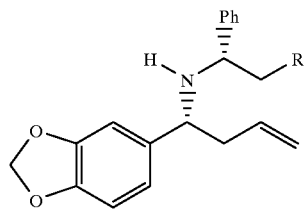

VII or diastereoisomer or salt form thereof, wherein R is H, OH, or $OCH_3$ and the diastereomeric excess obtained is at least 75%; and, (f) hydrogenating a compound of Formula VII or diastereomer or salt form thereof in the presence of palladium on carbon in a $C_{1-3}$ alcohol and a $C_{2-4}$ carboxylic acid to form a compound of Formula I or stereoisomer or salt form thereof;

provided that a cerium reagent is not present in step (e).

[19] In another preferred embodiment, the chiral methylbenzylamine in step (d) is S-phenyl glycinol and R is OH in steps (e) and (f)

[20] In another more preferred embodiment, in step (e) the diastereomeric excess obtained is at least 85%; and, in step (f) the alcohol is selected from methanol and ethanol and the acid is acetic acid and the ratio of alcohol to acid is from 10:1 to 1:10.

[21] In another even more preferred embodiment, in step (e) the diastereomeric excess obtained is at least 90%; and, in step (f) the alcohol is ethanol and the ratio of alcohol to acid is from 10:1 to 1:1.

[22] In another even more preferred embodiment, in step (e) the diastereomeric excess obtained is at least 90%; and, in step (f) the alcohol is methanol and the ratio of alcohol to acid is from 10:1 to 1:1.

[23] In another more preferred embodiment, tetrahydrofuran is used as solvent in step (e).

[24] In a third embodiment, the present invention provides novel compounds of formula IV:

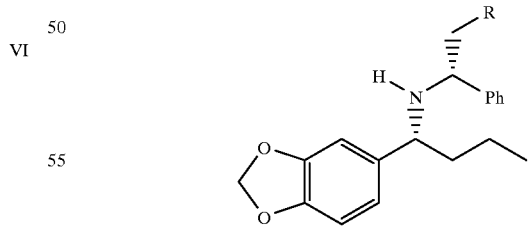

IV wherein R is selected from H, OH, and $OCH_3$, or stereoisomers or salt forms thereof.

[25] In another preferred embodiment, R is H.

[26] In another more preferred embodiment, the compound of formula IV is in the mandelic acid salt form.

[27] In a fourth embodiment, the present invention provides novel compounds of formula VII:

VII

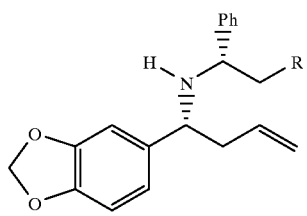

wherein R is selected from H, OH, and OCH₃, or stereoisomers or salt forms thereof.

[28] In another preferred embodiment, R is OH.
[29] In another more preferred embodiment, the compound of formula VII is in the tartaric acid salt form.

The reactions of the present synthetic methods are carried out in suitable solvents, unless otherwise specified which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

"Stable compound" and "stable structure" are meant to indicate a compound that is sufficiently robust to survive isolation to a useful degree of purity from a reaction mixture, and formulation into an efficacious therapeutic agent.

The compounds herein described may have asymmetric centers. All chiral, diastereomeric, and racemic forms are included in the present invention. Geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

Salt, as used herein, is intended to represent compounds which have been reacted with an organic, chiral or achiral, or inorganic acid. Chiral and achiral organic acids are well known in the art, examples include, but are not limited to, mandelic acid, tartaric acid, oxalic acid, and p-toluene sulfonic acid. Inorganic acids are well known in the art, examples included, but are not limited to, hydrochloric acid, phosphoric acid, and sulfuric acid.

As used herein, an alcohol is preferably a $C_{1-3}$ alcohol which is intended to represent methanol, ethanol, n-propanol, and i-propanol, preferably methanol or ethanol. A carboxylic acid or dicarboxylic acid is intended to represent a $C_{2-4}$ carboxylic or dicarboxylic acid; examples of which include, but are not intended to be limited to, acetic acid, propionic acid butyric acid, oxalic acid, malonic acid, and succinic acid, preferably acetic acid. Aromatic carboxylic acid is intended to represent carboxylic acids attached to a phenyl ring, for example, benzoic acid.

The ratio of alcohol to acid, as used herein, is intended to represent a volume to volume ratio.

Chiral methylbenzylamine, as used herein, is intended to represent either the R or S stereoisomer of the following structure:

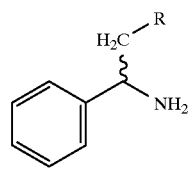

wherein R is H, OH, or OCH₃. Examples include, but are not intended to be limited to, R-α-methylbenzylamine, S-α-methylbenzylamine, S-phenyl glycinol, and R-phenyl glycinol, preferably, R-α-methylbenzylamine or S-phenyl glycinol.

Cerium reagent as used herein is intended to encompass cerium compounds known to those of skill in the art to be useful Lewis acid chelators in Grignard additions. Useful being defined as providing increased Grignard addition selectivity compared with reactions not using a cerium reagent. Such cerium reagents include inter alia cerium chloride and also organocerium reagents.

The present invention is contemplated to be practiced on at least a multigram scale, kilogram scale, multikilogram scale, and industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

High yield, as used herein, is intended to mean the overall yield of product from starting material is at least 45% of theoretical, preferably 50%, more preferably 55, and even more preferably 60.

Synthesis

By way of example and without limitation, the present invention may be further understood by Scheme 1 shown below. This scheme details the general synthetic method for preparation of the compound of Formula I or stereoisomer or pharmaceutical salts thereof from compounds of Formulae II and V.

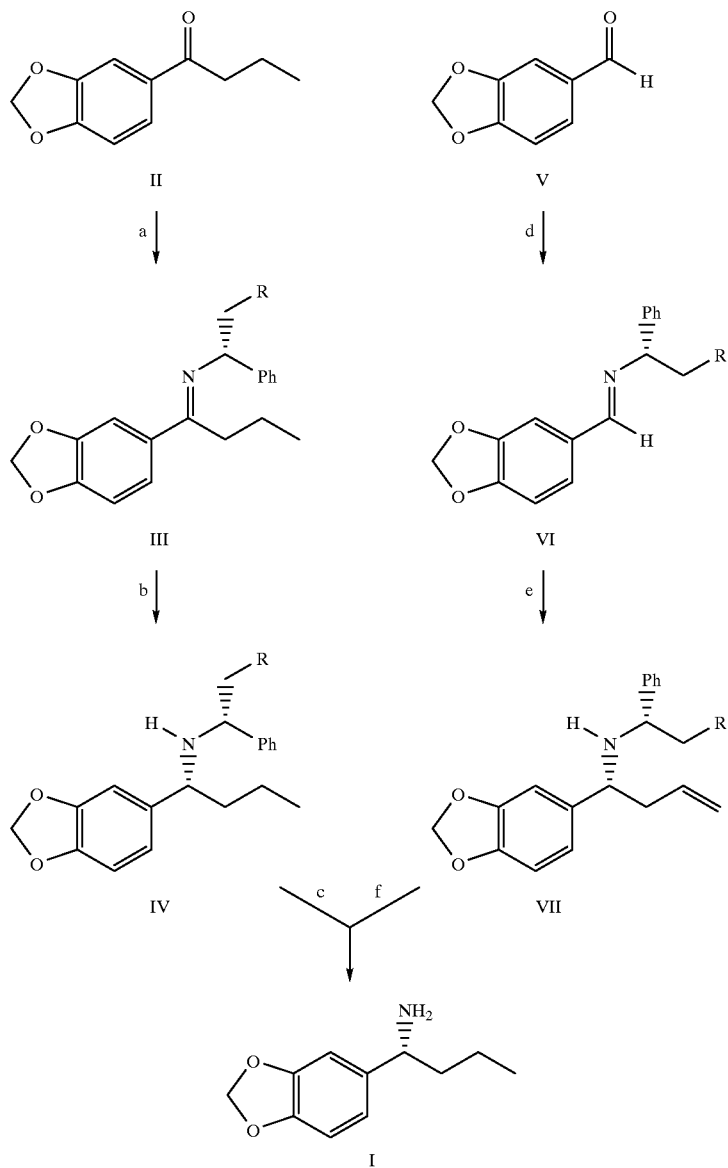

For compound I, the hydrochloride salt is Ia. For compound IV, the SR diastereomer is IVa, the mandelate salt is IVb and the hydrochloride salt is IVc. For compound VII, the tartrate salt is VIIa and the SS diastereomer is VIIb.

The above scheme (R=H, OH, or OCH$_3$) and following description relate to only R-α-propyl-piperonyl amine. However, as one of ordinary skill in the art would readily understand, the present invention can be used to for either the R or S enantiomers depending upon what enantiomer of the chiral amine is used in either step a or d. Thus, the above scheme and following description is not intended to be limited to R-α-propyl-piperonyl amine, but rather is intended to generally describe the synthesis of R and S-α-propyl-piperonyl amine.

In a first embodiment, the present invention contemplates a process for making a compound of Formula I via steps a, b, and c shown above.

Compound II can be made by known methods from known precursors. For example, 1,3-benzodioxole, which is available from Aldrich Chemical Company, can be readily converted to II by reaction with butyric anhydride in dichloroethane in the presence of gaseous BF$_3$.

Step a

Imine III can be formed from ketone with a chiral met II with a chiral methylbenzylamine in the presence of triethylamine, titanium tetrachloride and toluene under reflux conditions. Preferably, R-α-methylbenzylamine is used as the chiral amine. Those of ordinary skill in the art would understand that to obtain III when R is OH or OCH$_3$, the correspondingly substituted R-α-methylbenzylamine would need to be used. Preferably, at least a stoichiometric amount of chiral amine, based on the amount of ketone II, is used. An excess of chiral amine can be used to enhance yields or lower reaction times. Other water removal conditions known to those of skill in the art could be used to form Imine III from ketone II. A mixture of E and Z isomers of III is expected to be obtained, though the E isomer should dominate.

Step b

Selective hydrogenation of III to IV is obtained using Ra—Ni as catalyst. Preferably, from 1 to 15 wgt % of catalyst based on the amount of III present is used, more preferably, 5 to 10 wgt %, and even more preferably about 10 wgt %. A number of solvents can be used for this step including, but not limited to, tetrahydrofuran, methanol, ethanol, and toluene. Preferably, ethanol or methanol is used as solvent. Combinations of solvents may be used. For example, toluene and ethanol in a ratio of 1:9 may be used. Smaller or larger amounts of toluene may be used, e.g., 10:1 to 1:10, but generally the reaction slows as the amount of toluene increases.

Step b can be run at one temperature or at two temperatures and the temperature can range from −78 to 150° C., preferably 0 to 100° C. Preferably, when one temperature is used, it is from 0 to 70° C., more preferably from 20 to 60° C., and even more preferably ambient temperature or 50, 51, 52, 53, 54, 55, 56, 57, 58, 59, or 60° C. If one temperature is used, the hydrogen pressure is preferably in the range of 0.01–10 psi, more preferably 0.01–2 psi, and even more preferably 0.01–1 psi. Preferred reaction times, when one temperature is used, are from 2–30 hours, more preferred 3–24 hours, and even more preferred 3, 4, 5, 6, 7, 8, 9, 10, 11, or 12 hours.

The purpose behind using low hydrogen pressure (i.e., ≦10 psi) for the one temperature reduction is that the present inventors have found an increase in pressure causes a reduction in stereoselectivity. As will be further described in Example 1 below, a diastereoselectivity of 86 was achieved by hydrogenolysis with <1 psi of hydrogen at ambient temperature. In contrast, if the same conditions are used, but the hydrogen pressure is increased to 50 psi, the diastereoselectivity drops to only 75%.

Step b can also be run at one temperature under higher hydrogen pressures if the temperature is from 60 to 100° C., preferably 60 to 80° C., more preferably 60, 62, 64, 66, 68, 70, 72, 74, 76, 78, or 80° C. Hydrogen pressures of from 10–3000 psi, preferably 10–1000 psi, and more preferably from 50–500 psi can be used at these temperatures. Preferred reaction times, when one temperature is used, are from 2–30 hours, more preferred 3–24 hours, and even more preferred 3, 4, 5, 6, 7, 8, 9, 10, 11, or 12 hours. As noted above, high pressures of hydrogen can be advantageous as the catalyst load can be reduced compared with low pressure reactions.

When two temperatures are used, the reaction is run in two stages. The first stage is preferably run at 0 to 35° C., more preferably from 20 to 30° C., and even more preferably ambient temperature. The first stage is preferably run for 2–8 hours, more preferably 3–6 hours, and even more preferably from 3, 4, 5, or 6 hours. The second stage is preferably run at from 40 to 100° C., more preferably 60 to 80° C., even more preferably from 65 to 75° C., and still more preferably 65, 66, 67, 68, 69, 70, 71, 72, 73, 74, or 75° C. The second stage is preferably run for from 2–24 hours, more preferably from 6–18 hours, even more preferably from 10–15 hours, and still more preferably 10, 11, 12, 13, 14, or 15 hours. The hydrogen pressure is preferably in the range of 0.01–3000 psi, more preferably 50–500 psi, and even more preferably 100–300 psi. As one of ordinary skill in the art would recognize, it is preferable in industry to use hydrogen pressures greater than 10 psi. This allows for lower catalyst loading and simpler or at least more readily available apparatus, which saves money. Preferably, after running the first step, the reaction is heated to the temperature of the second step. Heat can be applied by methods known to those of skill in the art.

The present inventors have found that the high diastereoselectivity obtained by the present two temperature hydrogenation step can be attributed to the fact that the anti-imine of III is reduced much faster than syn-imine by Raney-Ni/H$_2$. As $K_{as}$ and $K_{sa}$ are very much temperature dependent, simply raising the temperature causes syn-imine to be isomerized to anti-imine which is then rapidly reduced. The following scheme illustrates this point.

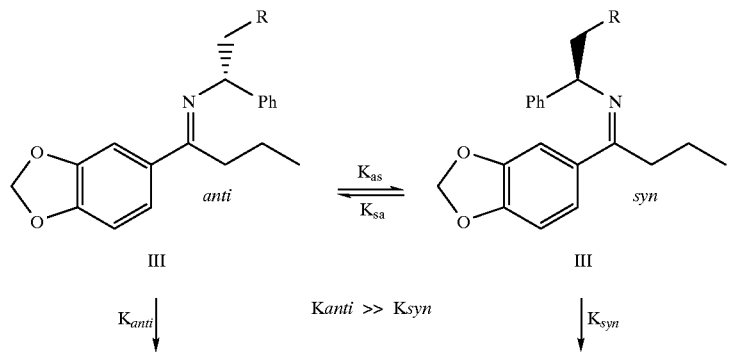

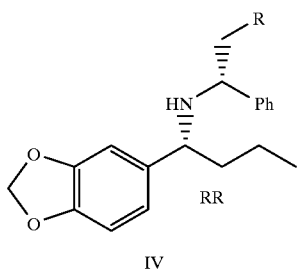

IV

-continued

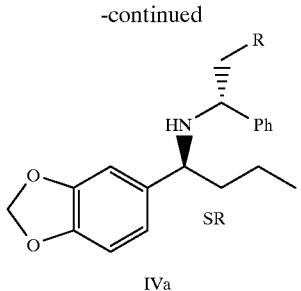

IVa

By initially running the hydrogenolysis reaction at near ambient temperatures, a majority of the anti-imine present is reduced. The temperature is then raised which promotes interconversion of the two isomers. As anti-imine is formed, it is rapidly reduced. Thus, high diastereoselectivity is obtained.

The diastereomeric excess de (RR vs SR for compounds IV and IVa, respectively) obtained in step c is preferably at least 80% (100% being the maximum), more preferably at least 85% and even more preferably at least 90%. Reaction times will depend upon a number of variables including hydrogen pressure, solvent, and temperature. The reaction can be monitored by standard HPLC techniques to determine when imine hydrogenation has been completed.

After formation of IV, its diastereomeric purity can be enhanced by formation of a salt with an organic acid. For example, crude or impure IV can be diastereomerically purified by dissolving in acetonitrile, introducing S-mandelic acid, and collecting the precipated mandelate salt. Other acids known to those of skill in the art including chiral and achiral acids (e.g., oxalic acid) as well as inorganic acids can be used as long as the resulting salt forms crystals.

Step c

Either the free base of IV or a salt thereof, i.e., the mandelic salt (IVc), can be used in step c. It is noted that certain salts limit the effectiveness of this step and should be avoided. For example, the HBr salt of IV is difficult to debenzylate and is preferably avoided. Since step c involves an additional hydrogenation step using a different catalyst, but similar solvents, it can be advantageous to avoid forming the salt and proceed directly with step c. Such a method allows one to minimize solvent usage and product loss due to crystallization. Preferably, catalyst is removed between each step to allow for catalyst recycling.

Conversion of IV to I can be achieved by hydrogenating IV, preferably at ambient temperatures, using Pd/C, preferably 10% Pd/C, as catalyst. Preferably, from 5 to 25 wgt % of catalyst based on the amount of IV present is used, more preferably, 10 to 20 wgt %, and even more preferably about 15 wgt %. Hydrogen pressure is preferably in the range of 0.01–1000 psi, more preferably 10–200 psi. As solvent, preferably a combination of an alcohol selected from methanol, ethanol and isopropyl alcohol and a carboxylic acid selected from acetic acid and propionic acid is used, more preferably ethanol and acetic acid or methanol and acetic acid. The alchols or acids can be used individually. The ratio of alcohol to acid preferably is from 30:1 to 1:10, more preferably from 30:1 to 1:1, and even more preferably from 20:1 to 8:1. It is also preferable to have from 1 to 4 equivalents of acid present based on the amount of IV, more preferably, 2 equivalents of acid. As with step b, reaction time will depend on how the above variables are chosen. The removal of phenethane can be monitored by standard HPLC techniques. Preferably, step c will be performed from 2 to 48 hours, more preferably, from 4 to 9 hours. The ee of I obtained in this step is preferably at least 70%, more preferably at least 85%.

Upon formation of I, it can be advantageous to form its HCl salt (Ia) to increase its ee. Compound I obtained after hydrogenation in the presence of palladium on carbon can be dissolved in toluene, isopropyl alcohol or a mixture thereof and its HCl salt precipitated by addition of either aqueous HCl or HCl in isopropyl alcohol. The enantiomeric excess (ee) of Ia can be further increased by reslurrying in isopropyl alcohol and n-heptane. Preferably, 5–6N HCl in isopropyl alcohol is added to a solution of I in toluene In a second embodiment, the present invention provides a process for making a compound of Formula I via steps d, e, and f shown above.

Step d

Compound V, piperonal, is known and available from Aldrich Chemical Company. Formation of imine VI can be accomplished by contacting V and an appropriate chiral amine under water removal conditions. Preferably, the reaction is run with S-phenyl glycinol (for when R=OH), p-toluenesulfonic acid, and toluene under reflux conditions with a Dean-Stark trap. Preferably, at least a stoichiometric amount of chiral amine, based on the amount of aldehyde, is used. An excess of chiral amine can be used to enhance yields or lower reaction times. Those of ordinary skill in the art would understand that to obtain VI when R is H or $OCH_3$, the corresponding methylbenzylamine would need to be used. Other water removal conditions known to those of skill in the art could be used. As with compound III, the E isomer of V is expected to dominate, thought both isomers are expected to be formed.

Step e

Using allylmagnesium chloride, which is available from Aldrich Chemical Company or can be made by methods known to those of skill in the art, VI can be converted to VII. This reaction proceeded with high diastereoselectivity and high yield (about 72–82%). The de obtained from this reaction is preferably at least 75%, more preferably at least 85%, and even more preferably at least 90%. At least stoichmetric amounts of the Grignard reagent, based on the imine, are needed. Preferably an excess of grignard is used to promote the reaction. For example, an excess of 1.5, 2, 2.5, 3, 3.5, 4, 4.5, 5, or more fold of grignard, preferably, 2.5 fold, can be used. Standard Grignard solvents which are known to those of skill in the art can be used for example, ethers as defined previouly, preferably, THF. The temperature preferred for the Grignard addition is between 20 and 30° C., more preferably near ambient conditions. Due to the nature of Grignard additions, it may be necessary to slowly add the Grignard reagent, cool the reaction, or both to maintain the preferred temperature. Reaction times are preferably from 1 to 5 hours, more preferably from 2–3 hours.

Preferably, Lewis acid chelators, such as cerium reagents (e.g., cerium chloride) are excluded from step (e). The present conditions allow for diastereoselective delivery of the allyl group without the need of Lewis acid chelators such as $ZnCl_2$, $TiCl_4$, $BF_3$—$O(Et)_2$, CuI, $CuBr_2$—$S(CH_3)_2$, and cerium reagents (e.g., $CeCl_3$) to enhance selectivity. For Grignard additions, cerium reagents are usually used as chelators to enhance selectivity. Unfortunately, cerium reagents are usually avoided in industry due to their difficult handling. Therefore, the present addition step, which avoids using cerium reagents, is superior to those described in the literature and noted in the present background section which require cerium or other Lewis acid chelators to enhance Grignard selectivity.

Upon formation of VII, its de can be enhanced by contacting it with an organic acid to form a salt which precipitates and can be easily isolated. For example, VII can be dissolved in acetonitrile, isopropyl alcohol or ethyl acetate, preferably acetonitrile and tartaric acid, oxalic acid or malic acid added, preferably tartaric acid. Preferably, the tartrate of VII is formed in acetonitrile as it readily precipitates from acetonitrile. The de of VII can also be enhanced by crystallization of the free base, preferably from ethyl acetate and n-heptane.

Neither propylmagnesium chloride nor propyl lithium are useful for this reaction. Propylmagnesium chloride resulted in a low yield, approximately 50%. Propyl lithium provided only about 60% de. Thus, neither of these reagents resulted in both desirable yields and diastereoselectivities.

Step f

Hydrogenation of VII in the presence of palladium on carbon, preferably 10% Pd/C, removes 2-phenethanol (R=OH) and produces I. Preferably, from 5 to 25 wgt % of catalyst based on the amount of VI present is used, more preferably, 10 to 20 wgt %, and even more preferably about 15 wgt %. Preferably the hydrogen pressure used is from 0.1 to 10 psi, more preferably from 1 to 5 psi, and even more preferably 2, 3, or 4 psi. Ambient temperature is preferred. Reaction progress can be monitored via HPLC. Preferred hydrogenation times are from 24 to 48 hours. As solvent, preferably a combination of an alcohol selected from methanol, ethanol and isopropyl alcohol and a carboxylic acid selected from acetic acid and propionic acid is used, more preferably ethanol and acetic acid or methanol and acetic acid. The ratio of alcohol to acid preferably is from 10:1 to 1:10, more preferably from 10:1 to 1:1, and even more preferably from 8:1 to 3:1. The olefin of the propenyl side is reduced very rapidly, leading to "reduced" VII which then undergoes debenzylation. Additional catalyst can be added to ensure complete conversion of VII to I.

Upon formation of I, it can be advantageous to form its HCl salt. Compound I obtained after hydrogenation in the presence of palladium on carbon can be dissolved in toluene, isopropyl alcohol or a mixture thereof and its HCl salt precipitated by addition of either aqueous HCl or HCl in isopropyl alcohol. The ee of I can then be increased by recrystallization from isopropyl alcohol and n-heptane. Preferably, 6N HCl in ispropyl alcohol is added to a solution of I in toluene. The resulting solid is then isolated.

Other features of the invention will become apparent in the course of the following descriptions of exemplary embodiments which are given for illustration fo the invention and are not intended to be limiting thereof.

EXAMPLES

Example 1

Step a

Preparation of (R)-N-[1-(1,3-Benzodioxol-5-yl) butylidene]-α-methylbenzene-methanamine (III) (R=H))

A 22 L reaction flask with overhead stirring, water condenser, nitrogen inlet, 2 L addition funnel, temperature probe was charge sequentially with II (R=H) (1 Kg, 5.2M), toluene (10 L), R-(+)-a-methylbenzyl amine (816 mL, 6.35M), and triethylamine (1836mL, 13.2M) and cooled to 5° C. A titanium(IV) chloride solution (320 mL in 1 L toluene) was added slowly through a 2 L addition funnel with vigorous stirring, while maintaining the temperature under 15° C. The addition took 1–2 hr. After the addition was complete, the reaction mass was stirred at room temperature for 1 hr and then heated to gentle reflux (111° C.) with vigorous stirring for 4 hours. The reaction mass was cooled to rt, filtered through celite to remove the solid ($TiO_2$ and $Et_3NHCl$) and the cake was washed with toluene (4 L). The toluene solution was washed with cold 10% NaOH (1×2.5 L) and saturated NaCl aqueous solution (2×2 L). The solution was dried over sodium sulfate and concentrated in vacuum to give an oil (1524 g, 96.2 wt %, yield 95%).

Step b

Preparation of [R-(R*, R*]-N-(1'-Phenylethyl-α-propyl-1,3-benzodioxole-5-methanamine (S)-α-hydroxybenzeneacetate (IVb) (R=H)

A slurry of III (R=H) (1459 g) and Ra—Ni (wet, 500 g) in 10 L of ethanol was hydrogenated by bubbling hydrogen through at rt for 5–16 hr and then at 50–60° C. for another 5 hr. The catalyst was filtered off and washed with ethanol (1.5 L). The filtrate was concentrated by a rotovap to give IV as an oil (1280 g) which was then crystallized with S-mandelic acid (836 g, 5.5M) in 6 L acetonitrile. The solid was filtered and washed with 2 L cold acetonitrile and 2 L of cold heptane to give IVb (1784 g, 99.4 wt %, yield 80%).

The stereoselectivity of step b was compared with procedures using different catalysts, temperatures, and hydrogen pressures. Ethanol was used as solvent in all cases except for D, wherein THF was used. The results are shown in Table 1.

TABLE 1

Stereoselectivity of imine reduction

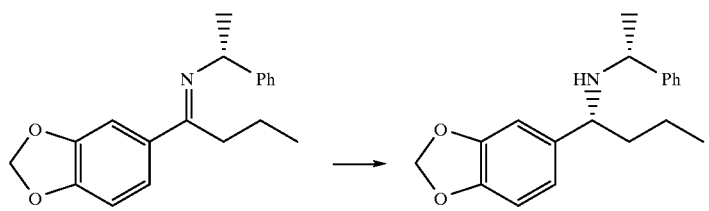

| | Catalysts | Temp (° C.) | H$_2$ (psi) | de | Note |
|---|---|---|---|---|---|
| 1 | Ra—Ni | 25 | <1 | 86 | |
| 2 | Ra—Ni | 55 | <1 | 89 | |
| 3 | Ra—Ni | 0–25 | <1 | 88 | |
| 4 | Ra—Ni | 25 & 65 | <1 | 94 | 5 h at 25 & 5 h at 65° C. |
| 5 | Ra—Ni | 23 & 70 | 150 | 91 | 6 h at 23 & 14 h at 70° C. |
| A | Ra—Ni | 25 | 50 | 75 | |
| B | NaBH$_4$ | −40–25 | — | 50 | |
| C | Pd/C | 25 | <1 | 67 | |
| D | Pd/C | 25 | <1 | 67 | |

As can be seen, hydrogenating under high pressure without high temperature (Comparative Example A) causes a more than two-fold loss of diastereoselectivity compared with the present invention. In addition, replacement of Ra—Ni with either Pd/C (Comparative Examples C and D) or NaBH$_4$ (Comparative Example B) also resulted in loss of diastereoselectivity.

Step b can also be performed without isolation of IV. Avoiding isolation of IV limits loss of product due to crystallization and also limits additional solvent needs.

Alternative Step b

Preparation of [R-(R*, R*]-N-(1'-Phenylethyl-α-propyl-1,3-benzodioxole-5-methanamine (IV) (R=H)

A slurry of III (15 g) and Ra—Ni (wet, 2.2 g) in 140 mL of ethanol was hydrogenated under hydrogen (150 psi) at rt for 6 hr and then at 70° C. for another 14 hr. The catalyst was filtered off and washed with ethanol (20 mL) to give a solution of IV (12.8 g, 85%) in about 150 mL ethanol.

Step c

Preparation of (R)-α-Propyl-1,3-benzodioxole-5-methanamine hydrochloride (Ia)

A 22 L reaction flask with overhead stirring, a dispersion tube and a thermocouple was charged sequentially with of IV (R=H) (1776 g), acetic acid (7 L), Pd/C(10%) (50% water) (450 g), and ethanol (7 L). Hydrogen gas was bubbled through for 24–26 hr with stirring and the catalyst was then filtered off. The filtrate was concentrated in vacuum to small volume and dissolved in toluene (10 L). The toluene solution was washed with 10% NaOH (1×10 L and 1×5 L) and water (3×3 L). Aq.conc.HCl (36–38%, 450 mL ) was then added and a slurry formed. Filtered the solid and washed the cake with cold toluene (2 L) to give Ia (R=H) (873 g, 99.4 wt %, 100 wt %, yield 96%).

A variety of conditions for step c were tested. The results of which are shown in Table 2 below.

TABLE 2

Stereoselective Debenzylation

| | Conditions | Conversion % | Note |
|---|---|---|---|
| 1 | Free base, EtOH/AcOH (8:1), 20 hr | 100 | |
| 2 | Free base, EtOH/AcOH (3:1), 20 hr | 100 | |
| 3 | Free base, EtOH, 20 hr | 87 | |
| 4 | Free base, AcOH, 20 hr | 82 | |
| 5 | Free base, AcOH/EtOH (1:1), 20 hr | 93 | |
| 6 | Free base, propionic acid/EtOH (1:1) | 100 | |
| 7 | Mandelate, AcOH/EtOH (1:1), 21 hr | 97.5 | |
| 8 | Free base, AcOH (2 eq)/EtOH (1:1), 7 hr | 100 | |
| A | Pd/C (10%), HCO$_2$NH$_4$/MeOH, reflux | 100 | partial racemization |
| B | HBr salt, AcOH/EtOH (1:1), 20 hr | <5 | |

Comparative Examples A and B were performed using the conditions described by Bringmann et al in *Leibigs Ann. Chem.* 1990, 795, page 799. As can be seen neither of these procedures were very useful as the resulting product was partially racemized (Comparative Example A) or an extremely low yield was obtained (Comparative Example B).

Example 2

Preparation of (R)-α-Propyl-1,3-benzodioxole-5-methanamine hydrochloride (Ia)

(R)-N-[1-(1,3-Benzodioxol-5-yl)butylidene]-α-methylbenzene-methanamine prepared according to step a of Example 1 from 500 g of II (R=H) and 816 ml of R-(+)-α-methylbenzylamine was dissolved in ethanol (6 L) with Ra—Ni (250 g, wet slurry) and hydrogenated at 23° C. for 5 hr and then at 60–65° C. for another 5 hr. The catalyst was filtered off and washed with ethanol (0.5 L). To the ethanol solution was added 0.5 L of acetic acid and Pd/C (10%)(50% water) (250 g). The hydrogen gas was bubbled through for 23 hr with stirring and the catalyst was then filtered off. The filtrate was concentrated in vacuum to small volume and dissolved in toluene (5 L). The toluene solution was washed with 10% NaOH (1×3 L and 1×2 L) and water (2×1.5 L). HCl in isopropyl alcohol (5–6N, 0.7 L) was then added and a slurry formed. Filtered the solid and washed the cake with cold toluene (2 L) to give the crude product (97.2% ee) which was relurried in isopropyl alcohol (2 L) and n-heptane (4 L). The solid was filtered and washed with n-heptane (2 L) to give Ia (R=H) (391.1 g, 99.1% ee).

Example 3 step d

Preparation of (R) -E-β-((1, 3-benzodioxol-5-ylmethylene)amino)benzene-ethanol (VI) (R=OH)

A solution of piperonal (2.3 Kg), (D)-phenylglycinol (2.1 Kg), and p-toluenesulfonic acid (2.5 g) in toluene (13 L) was heated to reflux using a Dean-Stark trap. Water separated at once and continued to separate throughout the reaction period. Once the theoretical amount of water was collected (over three to four hours), the reaction was analyzed by $^1$H-NMR. The reaction mass was cooled to about 80 to 85° C. Heptane (8 L) was added slowly, and the resulting solution cooled further to 5–10° C., and aged for about 1 hour. Precipitation was observed during the cooling period when the temperature was around 60° C. The product was isolated by filtration and dried under vacuum at 50 to 55° C. to constant weight, to provide 3.8 Kg of VI (R=OH) (95%) as a highly crystalline solid. $^1$H-NMR of this material is identical to that of an authentic sample.

step e

Preparation of (R)-β-(((1,3-benzodioxol-5-yl)-3-butenyl)amino)benzene-ethanol tartrate (VIIa) (R=OH)

A 2M solution of allylmagnesium chloride in THF (9.4L) was added to a cold solution (10–15° C.) of VI (R=OH) (2.02 Kg) in THF (9.5 L) dropwise over a period of about 2 hrs. The rate of addition was controlled to maintain the temperature below 30° C. The resulting mixture was aged for about 1.0 hr, cooled to 5 to 10° C., and quenched by slow addition to 30% aq acetic acid (14 L) while keeping the temperature below 30 °C. The organic phase was separated and treated with 20% aq NaOH solution, until the pH stabilized around 8. The layers were separated and the organic solution washed with 10% aq NaCl solution and concentrated to an oil under reduced pressure (89.5% de). To isolate as the tartrate salt, acetonitrile (15 L) was added followed by tartaric acid (1 eq., 1.1 Kg ). The mixture was warmed to 50–55 ° C., aged for about 1 hr, and slowly cooled to ambient temperature over a period of 2 to 4 hrs. After aging for 1 to 2 hrs at this temperature, the product was filtered, washed with acetonitrile (~10 L) and dried to constant weight under vacuum at 45–50° C. to yield VII-tartrate salt (R=OH) (2.6 Kg, 82%) as an off-white solid (98.8% de).

step f

Preparation of (R)-α-Propyl-1,3-benzodioxole-5-methanamine hydrochloride (Ia)

A degassed solution of VIIa (R=OH) (2.5 Kg) in methanol (9 L) and acetic acid (5 L) was pressure-transferred to a slurry of "wet" 10% palladium on carbon (~50% water content, 0.8 Kg) in methanol (9 L) and acetic acid (4.5 L). The resulting slurry was hydrogenated at 1 to 3 psi of hydrogen and ambient temperature for a period of 48 hrs. Samples were withdrawn for analysis. The progress of the reaction is followed by HPLC. Once the reaction was complete, the spent catalyst was removed by filtration and washed with methanol. The combined filtrates were concentrated under reduced pressure to a residue which was partitioned between toluene (4 L) and 1N aq. HCl soln.(~5 L). The aqueous phase was separated and basified to pH 13 with 30% aq. NaOH solution in the presence of toluene (7 L). The layers were separated and the aqueous layer extracted with toluene (5 L). The combined organic solutions were washed with 20% aq. NaCl, clarified through a Celite pad. The toluene solution was then cooled to 10–15° C. and a solution of 6N HCl in isopropanol (1.1 eqs.) was added slowly at such a rate to mantain the temperature below 20° C. The resulting slurry was aged for 1 hr at ambient temperature and then filtered. The solid was washed with toluene and dried in a vacuum oven at 50 to 55° C. to constant weight to provide 2.05 Kg (82% yield) of I as a white, fluffy solid with excellent enantiomeric purity (>99.5% ee) and wt % assay (>98% by HPLC).

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A process for the synthesis of a compound of Formula I:

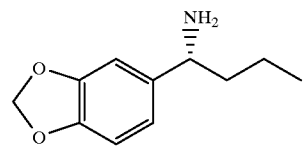

I or stereoisomer or salt form thereof, comprising:

(a) contacting a compound of Formula II:

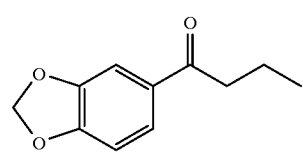

II with a chiral methylbenzylamine to form a compound of Formula III:

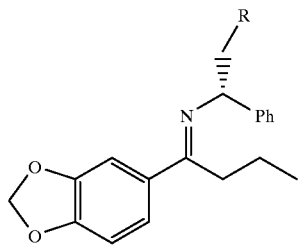

III or stereoisomer thereof, wherein R is selected from H, OH and OCH$_3$;

(b) hydrogenating a compound of Formula III of stereoisomer or salt thereof in the presence of Ra—Ni to form a compound of Formula IV:

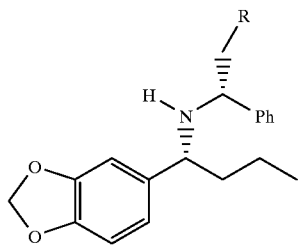

IV or diastereomer or salt form thereof, wherein the hydrogenation is performed under conditions selected from:

(bi) about 10–3000 psi at one temperature of from 60 to 80° C. for about 2–30 hours; or, (bii) about 0.01–3000 psi of hydrogen at a first temperature for about 2–8 hours and a second temperature for about 2–24 hours, the first temperature being from 0–35° C. and the second temperature being from 50–100° C.; and, (c) hydrogenating a compound of Formula IV or stereoisomer or salt form thereof in the presence of palladium on carbon and a solvent selected from an alcohol, a carboxylic acid, a dicarboxylic acid, an aromatic carboxylic acid and mixtures thereof to form a compound of Formula I or stereoisomer or salt form thereof;

provided that the compound of Formula IV hydrogenated in step c is not a hydrogen bromide salt.

2. A process according to claim 1, wherein in step (a), the chiral methylbenzylamine is R-α-methylbenzylamine, in step (b) R is H, and in step (c) R is H and the solvent is selected from a C$_{1-3}$ alcohol, a C$_{2-4}$ carboxylic acid, and mixtures thereof.

3. A process according to claim 2, wherein hydrogenation step (b) is performed under conditions (bi) under 10–1000 psi hydrogen at a temperature of from 60 to 80° C. for from 3–24 hours.

4. A process according to claim 3, wherein hydrogenation step (bi) is performed under 50–500 psi hydrogen.

5. A process according to claim 1, wherein hydrogenation step (b) is performed under conditions (bii); and, hydrogenation step (c) is performed in a mixture of a C$_{1-3}$ alcohol and a C$_{2-4}$ acid, wherein the alcohol and acid are present in a ratio of from 30:1 to 1:10.

6. A process according to claim 5, wherein hydrogenation step (bii) is performed under from 50–500 psi of hydrogen at a first temperature of from 20–30° C. for about 3–6 hours and a second temperature of from 60–80° C. for about 6–18 hours; and, in hydrogenation step (c), the alcohol is selected from methanol and ethanol, the acid is acetic acid, and the ratio of alcohol to acid is from 30:1 to 1:1.

7. A process according to claim 6, wherein hydrogenation step (bii) is performed under from 50–500 psi of hydrogen at a first temperature of from 20–30° C. for about 3–6 hours and a second temperature of from 60–80° C. for about 10–15 hours; and, in hydrogenation step (c), the alcohol is selected from methanol and ethanol, the acid is acetic acid, and the ratio of alcohol to acid is from 30:1 to 1:1.

8. A process according to claim 7, wherein hydrogenation step (bii) is performed under from 100–300 psi of hydrogen at a first temperature which is about ambient temperature for about 3, 4, 5, or 6 hours and a second temperature of from 65–75° C. for about 10, 11, 12, 13, 14, or 15 hours; and, hydrogenation step (c) is performed in ethanol and acetic acid in a ratio of from 20:1 to 8:1.

9. A process according to claim 7, wherein hydrogenation step (bii) is performed under from 100–300 psi of hydrogen at a first temperature which is about ambient temperature for about 3, 4, 5, or 6 hours and a second temperature of from 65–75° C. for about 10, 11, 12, 13, 14, or 15 hours; and, hydrogenation step (c) is performed in methanol and acetic acid in a ratio of from 20:1 to 8:1.

10. A process according to claim 5, wherein in step (c) about 1 to 4 equivalents of acid based on the amount of IV are present.

11. A process according to claim 5, wherein in step (c) about 2 equivalents of acid based on the amount of IV are present.

* * * * *